United States Patent
Yeh

(10) Patent No.: US 10,325,066 B2
(45) Date of Patent: Jun. 18, 2019

(54) SYSTEM FOR MENTAL HEALTH CLINICAL APPLICATION

(71) Applicant: Ta-Chuan Yeh, Taipei (TW)

(72) Inventor: Ta-Chuan Yeh, Taipei (TW)

( * ) Notice: Subject to any disclaimer, the term of this patent is extended or adjusted under 35 U.S.C. 154(b) by 205 days.

(21) Appl. No.: 15/626,609

(22) Filed: Jun. 19, 2017

(65) Prior Publication Data

US 2018/0011971 A1 Jan. 11, 2018

(30) Foreign Application Priority Data

Jul. 5, 2016 (TW) .............................. 105121182 A

(51) Int. Cl.
| | |
|---|---|
| *G06F 19/00* | (2018.01) |
| *G16H 50/30* | (2018.01) |
| *A63B 71/06* | (2006.01) |
| *A61M 21/00* | (2006.01) |
| *A63B 24/00* | (2006.01) |

(52) U.S. Cl.
CPC .......... *G06F 19/30* (2013.01); *A63B 71/0622* (2013.01); *G06F 19/00* (2013.01); *G16H 50/30* (2018.01); *A61M 21/00* (2013.01); *A61M 2021/005* (2013.01); *A61M 2021/0027* (2013.01); *A61M 2230/005* (2013.01); *A61M 2230/04* (2013.01); *A61M 2230/06* (2013.01); *A61M 2230/10* (2013.01); *A61M 2230/42* (2013.01); *A61M 2230/50* (2013.01); *A61M 2230/60* (2013.01); *A63B 2024/0012* (2013.01)

(58) Field of Classification Search
CPC ......... G06F 19/30; G06F 19/00; G16H 50/30; A63B 71/0622; A63B 2024/0012; A61M 21/00; A61M 2021/0027; A61M 2021/005; A61M 2230/005; A61M 2230/04; A61M 2230/06; A61M 2230/10; A61M 2230/42; A61M 2230/50; A61M 2230/60
See application file for complete search history.

(56) References Cited

U.S. PATENT DOCUMENTS

| | | | |
|---|---|---|---|
| 2016/0198996 A1* | 7/2016 | Dullen | A61B 5/0024 600/301 |
| 2016/0270656 A1* | 9/2016 | Samec | A61B 3/085 |
| 2018/0177426 A1* | 6/2018 | Xu | A61B 5/7275 |
| 2018/0292888 A1* | 10/2018 | Slepian | G06F 3/011 |
| 2019/0011703 A1* | 1/2019 | Robaina | G02B 27/01 |

* cited by examiner

*Primary Examiner* — Corbett B Coburn
(74) *Attorney, Agent, or Firm* — Michael Best & Friedrich LLP

(57) ABSTRACT

A system for mental health clinical application includes a virtual reality (VR) headset, a physiological sensor device and a computer device. The computer device is used to perform an illness test on a user by establishing a virtual 3D environment via the VR headset according to test data provided by the computer device. The computer device receives, from the physiological sensor device, a physiological signal of the user in response to the illness test to analyze an illness condition of the user.

7 Claims, 4 Drawing Sheets

SYSTEM FOR MENTAL HEALTH CLINICAL APPLICATION

FIELD

This application claims priority of Taiwanese Patent Application No. 105121182, filed on Jul. 5, 2016.

BACKGROUND

The disclosure relates to a system for mental health clinical application, and more particularly to a system for mental health clinical application which uses virtual reality (VR) technology.

A patient who has mental illness, such as social anxiety disorder (SAD), posttraumatic stress disorder (PTSD), obsessive-compulsive disorder (OCD), etc., may be unable to function normally in daily life.

Improvement of the mental illness may be achieved through psychotherapy. For example, exposure therapies may be used to treat anxiety disorders, such that the patient becomes less sensitive to a feared situation. In conventional exposure therapies, the patients may be asked to imagine a situation that they are afraid of, with or without assistance of sound or plane images, which has limited effects on immersing the patients in the situation.

SUMMARY

Therefore, the disclosure is to provide a system for mental health clinical application that provides a highly immersive environment for the patient to enhance illness evaluation or treatment effects.

According to this disclosure, the system includes a VR headset, a physiological sensor device and a computer device. The VR headset is configured to receive a VR data piece, and includes a display to establish a virtual 3D environment according to the VR data piece received thereby to be perceived by a user wearing the VR headset. The physiological sensor device is configured to sense a physiological signal of the user in response to perception of the virtual 3D environment. The computer device is coupled to the VR headset for data transmission therebetween, is coupled to the physiological sensor device for receiving the physiological signal therefrom, and is programmed to include an illness database, a VR object database, a test unit and an evaluation unit. The illness database is built with a plurality of illness data pieces, and a plurality of rating scales each of which corresponds to one of the illness data pieces. The VR object database is built with a first set of VR data pieces each corresponding to one of the rating scales. The test unit has a rating scale searching module to compare a first illness input of a description of an illness with the illness data pieces of the illness database for acquiring from the illness database at least one of the rating scales that corresponds to the first illness input; and a test execution module to execute an illness test by acquiring, from the VR object database, at least one of the VR data pieces which corresponds to one of the at least one rating scales obtained by the rating scale searching module, and transmitting the VR data pieces thus acquired to the VR headset. The evaluation unit has a reaction analysis module to perform quantitative analysis based on the physiological signal received from the physiological sensor device during execution of the illness test to generate test reaction level information; and an illness condition analysis module to obtain and output illness condition information according to the test reaction level information.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Figure 1:
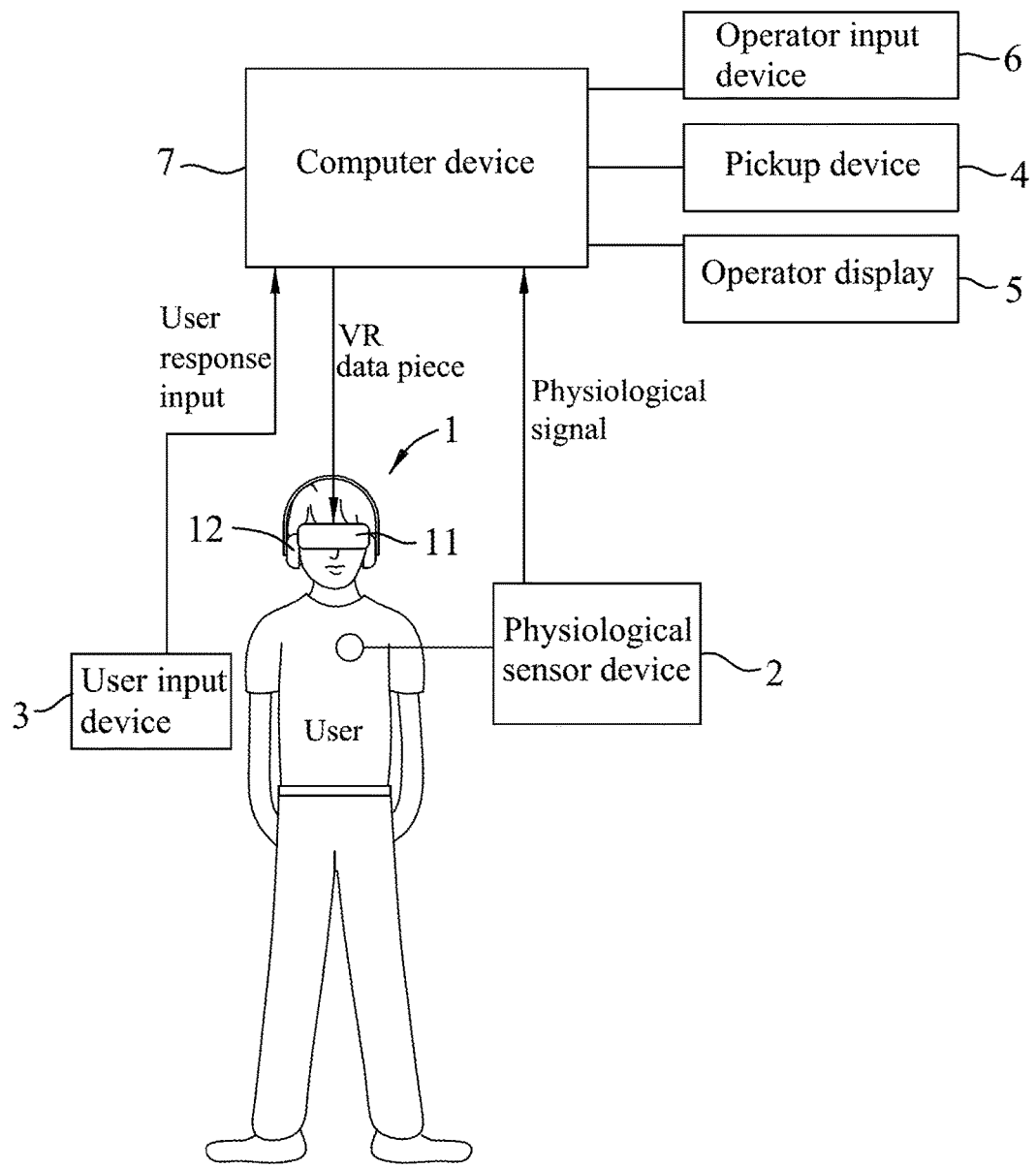
FIG. 1 is a schematic diagram illustrating an embodiment of the system for mental health clinical application according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
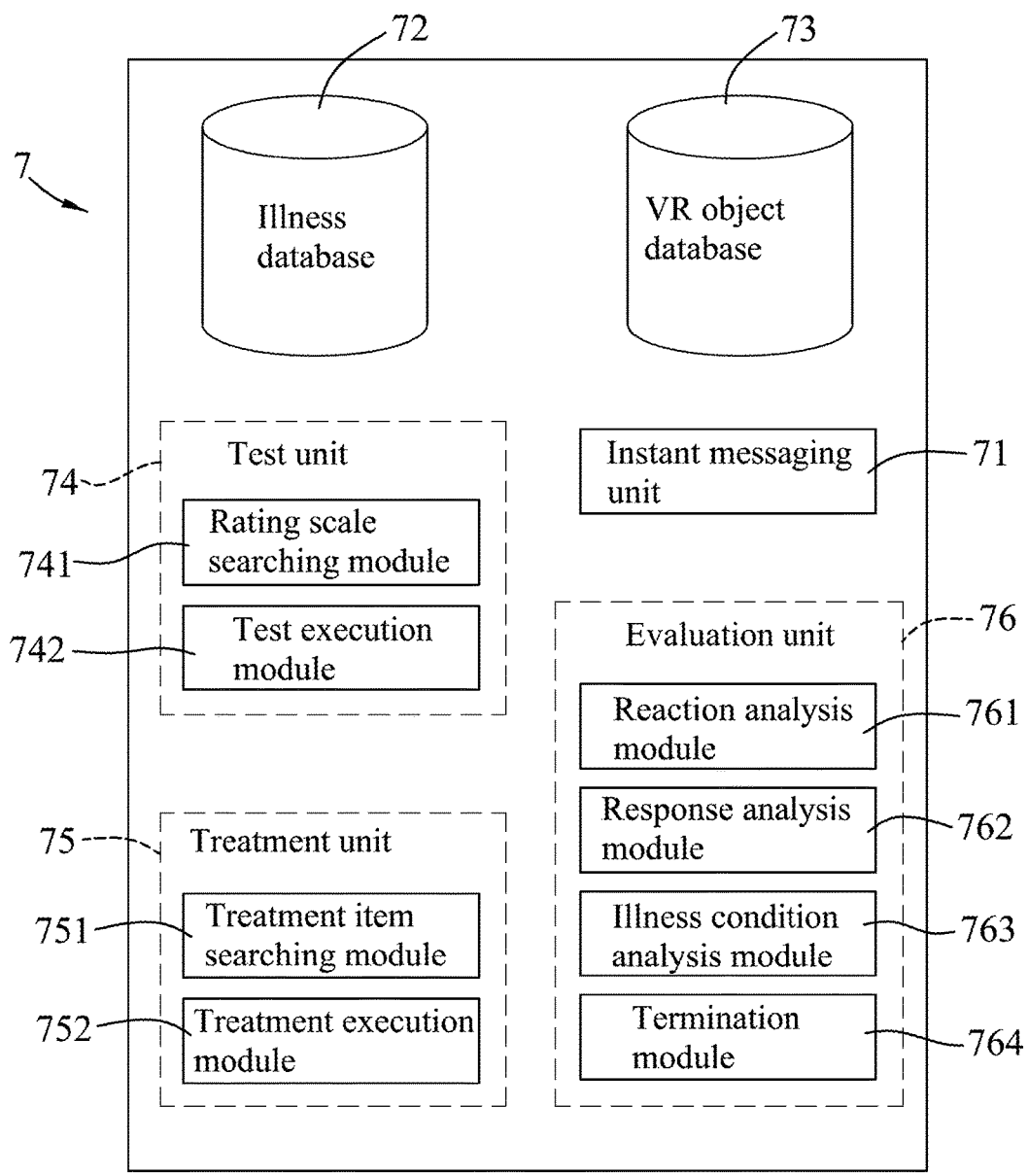
FIG. 2 is a block diagram illustrating architecture of a computer device of the embodiment.

Referring to FIGS. 1 and 2, the embodiment of the system for mental health clinical application is adapted for use by an operator (e.g., a doctor) to perform testing or treatment on a user (e.g., a patient who has mental illness), and includes a VR headset 1, a physiological sensor device 2, a user input device 3, a pickup device 4, an operator display 5, an operator input device 6 and a computer device 7.

The VR headset 1 is communicatively coupled to the computer device 7, is configured to be worn by the user and receive a VR data piece, and includes a display 11 and a headphone (e.g., earphone) 12 to establish a virtual 3D environment according to the VR data piece received thereby to be perceived by the user wearing the VR headset 1. Since the disclosure does not focus on techniques used by the VR headset 1 to generate the virtual 3D environment, details thereof are omitted herein for the sake of brevity.

The physiological sensor device 2 is communicatively coupled to the computer device 7, may include but not limited to, for example, electrocardiography (ECG) sensors, electroencephalography (EEG) sensors, electromyography (EMG) sensors, etc., to sense corresponding physiological signals of the user through several sensor electrodes attached to the user's skin, and performs pre-processing which may include but not limited to noise filtering, signal amplification, analog-to-digital conversion, etc., on the physiological signals. In some embodiments, the physiological sensor device 2 may include medical thermometers, electrodermal activity (EDA) sensors, respiratory rate sensors, heartbeat sensors, etc. to measure corresponding physiological signals of the user, and this disclosure is not limited in this respect.

The user input device 3 is communicatively coupled to the computer device 7 for the user to perform input operation while experiencing the virtual 3D environment, and to transmit data inputted by the user to the computer device 7. In practice, the user input device 3 may be communicatively coupled to the VR headset 1, and transmit data to the computer device 7 through the VR headset 1. The user input device 3 may be realized in a form of one or more hand controllers to be gripped by the user, one or more controller gloves, one or more touch panels, one or more voice recognition devices, one or more eye-tracking devices, one or more computer mice, one or more keyboards, one or more physical buttons, etc., or a combination of any of the above, but this disclosure is not limited thereto.

The pickup device 4, the operator input device 6 and the operator display 5 are communicatively coupled to the computer device 7 for the operator to operate the computer device 7. The pickup device 4 may include but not limited to a microphone to receive a voice message from the operator, and to output, to the computer device 7, a voice signal based on the voice message. The operator input device 6 may include but not limited to a computer mouse, a keyboard, a touch panel, etc., for the operator to input desired data, instructions, commands, etc. The operator display 5 may be but not limited to a general monitor, or a touch screen which is integrated with the operator input device 6 and which is configured to display information for the operator.

The computer device 7 may be realized by a personal computer or a remote server, and is programmed to include an instant messaging unit 71, an illness database 72, a VR object database 73, a test unit 74, a treatment unit 75 and an evaluation unit 76 in this embodiment. It is noted that, each of the instant messaging unit 71, the illness database 72, the VR object database 73, the test unit 74, the treatment unit 75 and the evaluation unit 76 may be realized as a combination of hardware, firmware and software and is configurable/programmable to implement operations that will be described hereinafter.

The instant messaging unit 71 is configured to provide the voice signal to the VR headset 1, so that the headphone 12 can output the voice message based on the voice signal to the user wearing the VR headset 1.

The illness database 72 is built with a plurality of illness data pieces, a plurality of rating scales each of which corresponds to one of the illness data pieces, and a plurality of treatment items each of which corresponds to one of the illness data pieces. Each of the illness data pieces may include information associated with a respective mental illness, such as social anxiety disorder, posttraumatic stress disorder, agoraphobia, etc., but this disclosure is not limited only to those mentioned above.

In this embodiment, each illness data piece may correspond to several rating scales, and each rating scale may include a plurality of test topics each being designed according to an illness data piece to which the rating scale corresponds. For example, the test topics that correspond to social anxiety disorder may be designed according to sources of stress with respect to different groups of people (e.g., different age groups, different genders); the test topics that correspond to posttraumatic stress disorder may be designed according to sources of stress with respect to different themes or events; and the test topics that correspond to agoraphobia may be designed according to sources of stress with respect to different environments. The test topics of the rating scales may be designed by a doctor or a therapist as desired, and the content thereof is not limited to those mentioned above.

In this embodiment, each illness data piece may correspond to several treatment items, and each treatment item may include a plurality of training topics each being designed according to an illness data piece to which the treatment item corresponds. For example, the training topics that correspond to social anxiety disorder may be designed according to treatments with respect to different groups of people; the training topics that correspond to posttraumatic stress disorder may be designed according to treatments with respect to different themes or events; and the training topics that correspond to agoraphobia may be designed according to treatments with respect to different environments. The training topics of the treatment items may be designed by a doctor or a therapist as desired, and the content thereof is not limited to those mentioned above.

The VR object database 73 is built with a first set of VR data pieces respectively corresponding to the test topics of the rating scales, and a second set of VR data pieces respectively corresponding to the training topics of the treatment items. Each VR data piece may include image files and/or audio files for establishing the virtual 3D environment. For example, the image files may include data to generate a virtual situation with vehicles, a crowd of people, or a confined space/room, and the audio files may include data to generate sound/voice of vehicles and/or people talking.

The test unit 74 has a rating scale searching module 741 and a test execution module 742. The rating scale searching module 741 compares a first illness input of a description of an illness, which is inputted by an input operation through the operator input device 6, with the illness data pieces in the illness database 72 to obtain an illness data piece corresponding to the first illness input (for example, the obtained illness data piece may contain information matching the description of the illness of the first illness input), and acquires, from the illness database 72, at least one of the rating scales that corresponds to the first illness input according to the obtained illness data piece (for example, correspondence may be found between each acquired rating scale and the obtained illness data piece). The operator display 5 displays the rating scale(s) thus acquired for the operator to select a desired rating scale from among that (those) displayed by the operator display 5 to perform an illness test on the user. The test execution module 742 executes the illness test by executing the test topics of the selected rating scale one by one. When the test execution module 742 executes one of the test topics of the selected rating scale, the test execution module 742 acquires a VR data piece which corresponds to said one of the test topics of the selected rating scale from the VR object database 73, for example by comparison (between the test topic and each VR data piece of the first set in, for example but not limited to, file names), and transmits the VR data piece thus acquired to the VR headset 1.

The treatment unit 75 has a treatment item searching module 751 and a treatment execution module 752. The treatment item searching module 751 compares a second illness input of a description of an illness, which is inputted by an input operation through the operator input device 6, with the illness data pieces of the illness database 72 to obtain an illness data piece corresponding to the second illness input (for example, the obtained illness data piece may contain information matching the description of the illness of the second illness input), and acquires from the illness database 72 at least one of the treatment items that corresponds to the second illness input according to the obtained illness data piece (for example, correspondence may be found between each acquired treatment item and the obtained illness data piece). The operator display 5 displays the treatment item(s) thus acquired for the operator to select a desired treatment item from among that (those) displayed by the operator display 5 to perform an illness treatment on the user. The treatment execution module 752 executes the illness treatment by executing the training topics of the selected treatment item one by one. When the treatment execution module 752 executes one of the training topics of the selected treatment item, the treatment execution module 752 acquires a VR data piece which corresponds to said one of the training topics of the selected treatment item from the VR object database 73, for example, by comparison (between the training topic and each VR data piece of the second set in, for example but not limited to, file names), and transmits the VR data piece thus acquired to the VR headset 1.

The evaluation unit 76 has a reaction analysis module 761, a response analysis module 762, an illness condition analysis module 763 and a termination module 764

When the test execution module 742 executes any one of the test topics, the reaction analysis module 761 receives the physiological signal(s) from the physiological sensor device 2, and performs quantitative analysis based on the physiological signal(s) to generate test reaction level information for the user with respect to the test topic. Similarly, when the treatment execution module 752 executes any one of the training topics, the reaction analysis module 761 receives the physiological signal(s) from the physiological sensor device 2, and performs quantitative analysis based on the physiological signal(s) to generate training reaction level information for the user with respect to the training topic. For instance, in a case that the physiological signal is an ECG signal, the reaction analysis module 761 may detect R-R intervals of the ECG signal to compute the heart rate, and use fast Fourier transform (FFT) to analyze the heart rate in the frequency domain. In this case, power under different frequency bands may serve as indices, wherein power in a low frequency band may serve as an index for functions of the sympathetic nervous system, power in a high frequency band may serve as an index for functions of the parasympathetic nervous system, and a power ratio of the low frequency band to the high frequency band or vice versa may be used to evaluate modulation between the sympathetic nervous system and the parasympathetic nervous system, which may represent a tension level of the user. The reaction analysis module 761 may classify the tension level of the user into scores to serve as the test reaction level information or the training reaction level information.

When the test execution module 742 executes any one of the test topics, the response analysis module 762 receives a user response input inputted in response to the experiencing of the virtual 3D environment, and performs analysis based on the user response input to generate response level information. For instance, one test topic may cause the VR headset 1 to establish a virtual 3D environment of a tunnel in which the user is located, and display a menu for the user to select a level of tension or fear about being in the tunnel from the menu, or to answer some well-designed questions associated with feeling of being in the tunnel, to serve as the user response input. The response analysis module 762 may analyze the selection or the answer of the user to determine the tension/fear level of the user with respect to being in the tunnel in a form of a score to serve as the test response level information.

The illness condition analysis module 763 analyzes the test reaction level information and the test response level information for all of the test topics of the selected rating scale to obtain illness condition information about the user and output the same through the operator display 5. For some test topics, the system may only request the user to answer questions for obtaining the test response level information, and does not measure the physiological signal(s) of the user so the test reaction level information is not obtained; for some test topics, the system may not request the user to answer any question so the test response level information is not obtained and only measures the physiological signal(s) of the user for obtaining the test reaction level information; and for some test topics, the system may both request the user to answer questions, and measure the physiological signal(s) of the user, so as to obtain both of the test reaction level information and the test response level information. The illness condition analysis module 763 may take the test reaction level information or the test response level information of a test topic as a score for that test topic. For a test topic for which both of the test reaction level information and the test response level information are obtained, the illness condition analysis module 763 may make an average of the test reaction level information and the test response level information, which are in the form of scores, the score for the test topic. Then, the illness condition analysis module 763 may obtain the illness condition information by summing up the scores for the test topics of the selected rating scale. In one embodiment, when a difference between the test reaction level information and the test response level information is greater than a predetermined threshold, which may represent inaccuracy of the user's response, the illness condition analysis module 763 may further output a message through the operator display 5 to notify that the result for the test topic may have relatively low reliability.

In this embodiment, the test topics may be divided into different sets respectively corresponding to different sources of stress to test the user's reaction with respect to different sources of stress. In one example, a rating scale that corresponds to agoraphobia may include a first set of test topics associated with a crowd of people, a second set of test topics associated with a situation of being in a tunnel, and a third set of test topics associated with a confined bedroom. The illness condition analysis module 763 may, for each individual set of test topics, sum up the scores for the corresponding test topics, so as to obtain the illness condition of the user with respect to the respective source of stress.

During execution of the illness treatment or the illness test, the termination module 764 may cause the treatment execution module 752 to terminate execution of the illness treatment when the training reaction level information is out of a predetermined reaction level range, or cause the test execution module 742 to stop execution of the illness test when the test reaction level information is out of the predetermined reaction level range.

Figure 3:
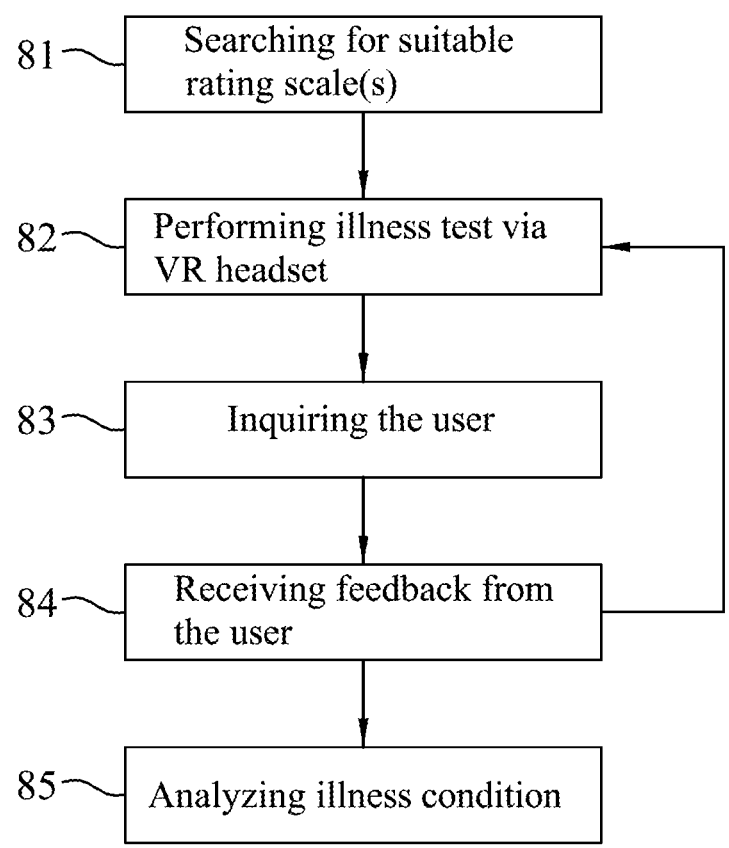
FIG. 3 is a flow chart of an exemplary illness test.
Figure 4:
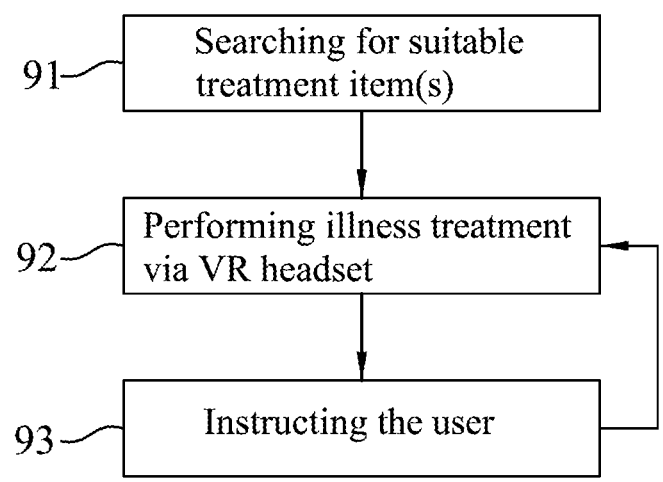
FIG. 4 is a flow chart of an exemplary illness treatment.

Referring to FIGS. 1-3, after the user wears the VR headset 1 and is attached with the sensor electrodes, the illness test may be performed by the following steps 81-85, where the illness to be tested for the user is assumed to be agoraphobia.

Step 81: The operator uses the operator input device 6 to activate the test unit 74, and input the first illness input (e.g., a name of an illness corresponding to the user, such as agoraphobia), into the computer device 7. The test unit 74 will search for the rating scale(s) that correspond(s) to the first illness input, and cause the operator display 5 to display the rating scale(s) thus located.

Step 82: The operator uses the operator input device 6 to select a rating scale suitable for the user, and the test unit 74 executes one of the test topics of the selected rating scale. During execution of the test topic, the test unit 74 acquires a VR data piece corresponding to the test topic from the VR object database 73, and transmits the acquired VR data piece to the VR headset 1 for the user to experience a corresponding virtual 3D environment.

In practice, the test unit 74 may transmit the VR data piece that causes the VR headset 1 to establish a virtual 3D environment with crowded people and noises to immerse the user in the virtual 3D environment, so as to trigger emotion of anxiety, fear or panic from the user more effectively.

Step 83: While the user is experiencing the virtual 3D environment, the operator uses the pickup device 4 to provide verbal messages to the VR headset 1 for inquiring the user. The operator may ask the user for example "How do you feel right now? Not nervous, slightly nervous, nervous, or very nervous?", and the VR headset 1 may simultaneously display the four options in the virtual 3D environment. In one embodiment, the operator may not need to speak, and can directly cause the VR headset 1 to display the above messages in the virtual 3D environment by text, and this disclosure is not limited thereto.

Step 84: The user may use the user input device 3 to respond to the operator's inquiry about his/her experience in the virtual 3D environment (i.e., the user response input). The evaluation unit 76 receives and analyzes the user response input according to the test topic to generate the test response level information. The evaluation unit 76 may also receive the physiological signal(s) of the user sensed by the physiological sensor 2 at the same time, and perform quantitative analysis on the physiological signal(s) to generate the test reaction level information and output the same.

In one exemplary implementation, if the user feels very uncomfortable about the virtual 3D environment of crowded people, the user may use a touch panel to select option "very nervous", which corresponds to a score of four points, and the evaluation unit 76 thus acquires the test response level information being four points. At the same time, the evaluation unit 76 receives and performs analysis on, for example, the ECG signal of the user from the physiological sensor device 2 in the frequency domain, so as to acquire the test reaction level information that is, for example, four points, which corresponds to a mental state of "very nervous", and execution of the test topic is completed. Then, the flow may go back to step 82 for execution of the next test topic of the selected rating scale. Steps 82 to 84 may be repeated for different test topics until execution of all of the test topics of the selected rating scale has been completed.

Step 85: The evaluation unit 76 analyzes the test reaction level information and the test response level information for the test topics to generate the illness condition information. In one exemplary implementation where the test topics are divided into three test topic sets respectively associated with three sources of stress, such as the crowded people situation, the tunnel situation and the confined bedroom situation, the evaluation unit 76 may add up, for each topic set, the scores of the corresponding test topics. For example, the illness condition level scores for the crowded people situation, the tunnel situation and the confined bedroom situation may be ten points, eight points and five points, respectively, and the evaluation unit 76 causes the operator display 5 to display these scores and a final illness condition information, so the operator may instantly be aware of the severity of agoraphobia of the user. The operator may record the final illness condition information for a research purposes, or for comparison with an illness condition obtained through an illness test performed in the future to assess the effect of the treatment.

Referring to FIGS. 1-4, after the user wears the VR headset 1 and is attached with the sensor electrodes, the illness treatment may be performed by the following steps 91-93, where the illness to be treated for the user is assumed to be agoraphobia.

Step 91: The operator uses the operator input device 6 to activate the treatment unit 75, and input the second illness input (e.g., a name of an illness corresponding to the user, such as agoraphobia), into the computer device 7. The treatment unit 75 will search for the treatment item(s) that correspond(s) to the second illness input, and cause the operator display 5 to display the treatment item(s) thus located. The treatment item(s) may focus on the confined bedroom situation, the tunnel situation, and/or the crowded people situation, and so on.

Step 92: The operator uses the operator input device 6 to select a treatment item suitable for the user according to the illness condition information obtained from the illness test, and the treatment unit 75 executes one of the training topics of the selected treatment item. During execution of the training topic, the treatment unit 75 acquires a VR data piece corresponding to the training topic from the VR object database 73, and transmits the acquired VR data piece to the VR headset 1 for the user to experience the corresponding virtual 3D environment.

In an example where the user has a relatively good illness condition (e.g., the illness condition level scores for the crowded people situation, the tunnel situation and the confined bedroom situation are ten points, eight points and five points, respectively) with respect to the confined bedroom situation, the operator may first select the treatment item associated with the confined bedroom situation to perform the illness treatment. The treatment unit 75 may transmit the VR data piece that causes the VR headset 1 to establish a virtual 3D environment of a confined bedroom in which the user is exposed, achieving effects of exposure therapies.

Step 93: When the user is immersed in the virtual 3D environment, the operator may use the pickup device 4 to provide voice messages for helping the user relax by for example instructing the user to follow a particular rhythm of breathing or to pay attention to particular objects in the virtual 3D environment. The flow may go back to step 92 for executing a next training topic. Steps 92 and 93 may be repeated for different training topics of the selected treatment item. After completion of all of the training topics of the selected treatment item (e.g., associated with the confined bedroom situation), the operator may use the operator input device 6 to select another treatment item, such as a treatment item associated with the tunnel situation. After completion of all of the training topics of the selected treatment item associated with the tunnel situation, the operator may use the operator input device 6 to select yet another treatment item, such as a treatment item associated with the crowded people situation. By causing the user to face the feared situations in the sequence from weak to severe, the user may gradually alleviate his/her anxiety.

During the illness test or the illness treatment, if the user is too nervous or anxious such that the reaction level analyzed by the evaluation unit 76 is out of the predetermined reaction level range, the evaluation unit 76 causes the test execution module 74 or the treatment execution module 75 to stop execution of the illness test or the illness treatment, protecting the user from excessive stress.

In summary, the system for mental health clinical application according to this disclosure facilitates the operator (e.g., a doctor) to find a desired rating scale corresponding to the illness of the user (e.g., a patient) via the computer device 7, provides the user with a virtual 3D environment to be immersed in via the VR headset 1, and analyzes the illness condition based on the physiological signal(s) and/or the response of the user through the cooperation among modules implemented in the computer device 7, the VR headset 1 and the physiological sensor device 2. During the illness treatment, the system also facilitates the operator (e.g., a doctor) to find a desired treatment item corresponding to the illness of the user, and provides a virtual 3D environment to help achieve better effect of exposure therapies. In addition, the computer device 7 may monitor the physiological signal(s) of the user measured by the physiological device 2 during the illness test or the illness treatment, and can automatically terminate the test or the treatment when the user is too anxious or nervous, promoting safety.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A system for mental health clinical application, comprising:
    a virtual reality (VR) headset that is configured to receive a VR data piece, that includes a display, and that establishes a virtual 3D environment according to the VR data piece received thereby to be perceived by a user wearing said VR headset;
    a physiological sensor device that is configured to sense a physiological signal of the user in response to perception of the virtual 3D environment; and
    a computer device that is coupled to said VR headset for data transmission therebetween, that is coupled to said physiological sensor device for receiving the physiological signal therefrom, and that is programmed to include:
    an illness database which is built with a plurality of illness data pieces, and a plurality of rating scales each of which corresponds to one of the illness data pieces;
    a VR object database which is built with a first set of VR data pieces each corresponding to one of the rating scales;
    a test unit which has:
        a rating scale searching module to compare a first illness input of a description of an illness with the illness data pieces of said illness database for acquiring from said illness database at least one of the rating scales that corresponds to the first illness input; and
        a test execution module to execute an illness test by acquiring, from said VR object database, at least one of the VR data pieces which corresponds to one of the at least one rating scales obtained by said rating scale searching module, and transmitting the at least one of the VR data pieces thus acquired to said VR headset; and
    an evaluation unit that has:
        a reaction analysis module to perform quantitative analysis based on the physiological signal received from said physiological sensor device during execution of the illness test to generate test reaction level information; and
        an illness condition analysis module to obtain and output an illness condition information according to the test reaction level information.

2. The system of claim 1, wherein each of the rating scales includes a plurality of test topics each corresponding to a respective one of the VR data pieces in the first set;
    wherein, during execution of the illness test, said test execution module executes the test topics of the one of the at least one of the rating scales obtained by said rating scale searching module one by one;
    wherein, when said test execution module executes one of the test topics of the one of the at least one of the rating scales obtained by said rating scale searching module, said test execution module acquires one of the VR data pieces that corresponds to said one of the test topics from said VR object database, and transmits said one of the VR data pieces that corresponds to said one of the test topics to said VR headset;
    wherein, when said test execution module executes one of the test topics of the one of the at least one of the rating scales obtained by said rating scale searching module, said reaction analysis module performs quantitative analysis based on the physiological signal to generate the test reaction level information for said one of the test topics; and
    wherein, after said test execution module has executed all of the test topics of the one of the at least one of the rating scales obtained by said rating scale searching module, said illness condition analysis module obtains and outputs the illness condition information according to the test reaction level information generated for all of the test topics of the one of the at least one of the rating scales obtained by said rating scale searching module.

3. The system of claim 2, further comprising a user input device configured to allow a user to perform input operation when experiencing the virtual 3D environment, and to transmit data inputted by the user to said computer device;
    wherein said evaluation unit further has a response analysis module to receive, from said user input device, a user response input inputted in response to experiencing of the virtual 3D environment when said test execution module executes one of the test topics of the one of the at least one of the rating scales obtained by said rating scale searching module, and to perform analysis based on the user response input to generate response level information; and
    wherein, after said test execution module has executed all of the test topics of the one of the at least one of the rating scales obtained by said rating scale searching module, said illness condition analysis module obtains and outputs the illness condition information according to the test reaction level information and the response level information which are generated for all of the test topics of the one of the at least one of the rating scales obtained by said rating scale searching module.

4. The system of claim 2, wherein said illness database is further built with a plurality of treatment items each corresponding to one of the illness data pieces and having a plurality of training topics;
    wherein said VR object database is further built with a second set of VR data pieces respectively corresponding to said training topics of the treatment items;

wherein said computer device is further programmed to include a treatment unit that has:

a treatment searching module to compare a second illness input of a description of an illness with the illness data pieces of said illness database for acquiring from said illness database at least one of the treatment items that corresponds to the second illness input; and a treatment execution module to execute an illness treatment by acquiring, from said VR object database, at least one of the VR data pieces which corresponds to one of the at least one treatment items obtained by said treatment searching module, and transmitting the at least one of the VR data pieces thus acquired to said VR headset;

wherein, during execution of the illness treatment, said treatment execution module executes the training topics of one of the at least one of the treatment items obtained by said treatment searching module one by one; and wherein, when said treatment execution module executes one of the training topics of one of the at least one of the treatment items obtained by said treatment searching module, said treatment execution module acquires one of the VR data pieces that corresponds to said one of the training topics of one of the at least one of the treatment items obtained by said treatment searching module, and transmits said one of the VR data pieces that corresponds to said one of the training topics from said VR object database to said VR headset.

5. The system of claim 4, wherein, when said treatment execution module executes one of the training topics of one of the at least one of the treatment items obtained by said treatment searching module, said reaction analysis module performs quantitative analysis based on the physiological signal to generate training reaction level information for said one of the training topics; and wherein said evaluation unit further includes a termination module to cause said treatment execution module to terminate execution of the illness treatment when the training reaction level information is out of a predetermined reaction level range, and to cause said test execution module to stop execution of the illness test when the test reaction level information is out of the predetermined reaction level range.

6. The system of claim 4, further comprising:

an operator display coupled to said computer device, wherein said rating scale searching module is configured to cause said operator display to display the at least one of the rating scales that corresponds to the first illness input, and said treatment searching module is configured to cause said operator display to display the at least one of the treatment items that corresponds to the second illness input; and an operator input device coupled to said computer device, and configured for an operator to input the first illness input and the second illness input, and to select a desired one of the rating scales from the at least one of the rating scales that is displayed by said operator display, and a desired one of the treatment items from the at least one of the treatment items that is displayed by said operator display.

7. The system of claim 1, further comprising a pickup device coupled to said computer device, and configured to receive a voice message from an operator, and to output to said computer device a voice signal based on the voice message;

wherein said computer device is further programmed to include an instant messaging unit to provide the voice signal to said VR headset;

wherein said VR headset further includes a headphone to output the voice message based on the voice signal to the user wearing said VR headset.

* * * * *